US009835595B2

(12) United States Patent
Webster et al.

(10) Patent No.: US 9,835,595 B2
(45) Date of Patent: Dec. 5, 2017

(54) SENSORS, METHODS OF MAKING AND DEVICES

(71) Applicant: Qorvo US, Inc., Greensboro, NC (US)

(72) Inventors: James Russell Webster, Minnetonka, MN (US); Peter J. Schiller, Coon Rapids, MN (US); Richard Allan Van Deusen, St. Paul, MN (US); Ian Robert Harmon, Minneapolis, MN (US)

(73) Assignee: QORVO US, INC., Greensboro, NC (US)

( * ) Notice: Subject to any disclaimer, the term of this patent is extended or adjusted under 35 U.S.C. 154(b) by 0 days.

(21) Appl. No.: 14/893,395

(22) PCT Filed: May 23, 2014

(86) PCT No.: PCT/US2014/039397
§ 371 (c)(1),
(2) Date: Nov. 23, 2015

(87) PCT Pub. No.: WO2014/190292
PCT Pub. Date: Nov. 27, 2014

(65) Prior Publication Data
US 2016/0116444 A1    Apr. 28, 2016

Related U.S. Application Data

(60) Provisional application No. 61/826,884, filed on May 23, 2013.

(51) Int. Cl.
*G01N 15/06*    (2006.01)
*G01N 33/00*    (2006.01)
(Continued)

(52) U.S. Cl.
CPC ......... *G01N 29/2437* (2013.01); *C23C 16/06* (2013.01); *C23C 16/45525* (2013.01);
(Continued)

(58) Field of Classification Search
CPC ........ G01N 15/06; G01N 33/00; G01N 33/48; G01N 33/543; G01N 33/546
(Continued)

(56) References Cited

U.S. PATENT DOCUMENTS 4,361,026 A    11/1982    Muller et al.
4,596,697 A *   6/1986    Ballato .......................... 422/98
(Continued)

FOREIGN PATENT DOCUMENTS

WO    WO 2005/050164 A2    6/2005
WO    WO 2014/143680 A1    9/2014
(Continued)

OTHER PUBLICATIONS

U.S. Appl. No. 13/162,353, filed Jun. 16, 2011, Van Deusen et al.
(Continued)

*Primary Examiner* — Brian J Sines
(74) *Attorney, Agent, or Firm* — Mueting, Raasch & Gebhardt, P.A.

(57) ABSTRACT

Disclosed sensors can include at least one resonator (in some embodiments, at least two resonators) and various other structures that may be formed in association with the resonators. The at least one resonator in embodiments can include a bottom electrode, a piezoelectric layer, and a top electrode, wherein the piezoelectric layer is positioned between the bottom electrode and the top electrode.

13 Claims, 5 Drawing Sheets

(51) Int. Cl.

| | | |
|---|---|---|
| *G01N 33/48* | (2006.01) | |
| *G01N 29/24* | (2006.01) | |
| *G01N 29/02* | (2006.01) | |
| *C23C 16/06* | (2006.01) | |
| *C23C 16/455* | (2006.01) | |
| *G01N 29/036* | (2006.01) | |
| *G01N 33/543* | (2006.01) | |
| *G01N 29/30* | (2006.01) | |

(52) U.S. Cl.
CPC ......... *G01N 29/022* (2013.01); *G01N 29/036* (2013.01); *G01N 29/30* (2013.01); *G01N 33/54373* (2013.01); *G01N 2291/014* (2013.01); *G01N 2291/0255* (2013.01); *G01N 2291/0256* (2013.01); *G01N 2291/0257* (2013.01); *G01N 2291/0426* (2013.01)

(58) Field of Classification Search
USPC ........ 422/82.01, 68.1, 98; 436/43, 518, 524, 436/525, 149
See application file for complete search history.

(56) References Cited

U.S. PATENT DOCUMENTS

| | | | |
|---|---|---|---|
| 4,654,127 A | | 3/1987 | Baker et al. |
| 4,735,906 A | * | 4/1988 | Bastiaans ............... 436/527 |
| 4,789,804 A | * | 12/1988 | Karube et al. ........... 310/311 |
| 4,847,193 A | * | 7/1989 | Richards et al. ......... 435/6.19 |
| 4,999,284 A | * | 3/1991 | Ward et al. ................ 435/4 |
| 5,404,628 A | | 4/1995 | Ketcham |
| 5,405,510 A | | 4/1995 | Betts et al. |
| 5,501,986 A | * | 3/1996 | Ward et al. ............... 436/525 |
| 5,693,233 A | | 12/1997 | Schembri |
| 5,821,833 A | | 10/1998 | Lakin |
| 5,894,647 A | | 4/1999 | Lakin |
| 5,922,591 A | | 7/1999 | Anderson et al. |
| 5,932,953 A | | 8/1999 | Drees et al. |
| 5,936,150 A | | 8/1999 | Kobrin et al. |
| 5,942,958 A | | 8/1999 | Lakin |
| 6,107,721 A | | 8/2000 | Lakin |
| 6,114,635 A | | 9/2000 | Lakin et al. |
| 6,235,488 B1 | | 5/2001 | Tom-May et al. |
| 6,291,931 B1 | | 9/2001 | Lakin |
| 6,441,703 B1 | | 8/2002 | Panasik |
| 6,686,128 B1 | | 2/2004 | Lakin et al. |
| 6,720,844 B1 | | 4/2004 | Lakin |
| 7,241,421 B2 | | 7/2007 | Webster et al. |
| 7,288,229 B2 | | 10/2007 | Turner et al. |
| 7,353,695 B2 | | 4/2008 | Fitch et al. |
| 7,419,821 B2 | | 9/2008 | Davis et al. |
| 7,468,138 B2 | | 12/2008 | Weinberg et al. |
| 7,666,687 B2 | | 2/2010 | Webster et al. |
| 7,695,681 B2 | | 4/2010 | Wang et al. |
| 7,871,569 B2 | * | 1/2011 | Zhang et al. ............ 422/68.1 |
| 7,963,151 B2 | | 6/2011 | Godfrey et al. |
| 8,066,944 B2 | | 11/2011 | Carter et al. |
| 8,084,002 B2 | | 12/2011 | Carter et al. |
| 8,154,093 B2 | | 4/2012 | Bradley et al. |
| 8,309,039 B2 | | 11/2012 | Webster et al. |
| 8,309,364 B2 | | 11/2012 | Miller et al. |
| 8,409,875 B2 | | 4/2013 | Johal et al. |
| 8,450,131 B2 | * | 5/2013 | Savoy et al. ............. 438/49 |
| 9,032,782 B1 | | 5/2015 | Van Deusen et al. |
| 2004/0262162 A1 | | 12/2004 | Roach et al. |
| 2006/0054941 A1 | | 3/2006 | Lu et al. |
| 2006/0160144 A1 | * | 7/2006 | Fendler ................. 435/7.1 |
| 2009/0017491 A1 | | 1/2009 | Lemme et al. |
| 2010/0127600 A1 | | 5/2010 | Loschonsky et al. |
| 2010/0218353 A1 | | 9/2010 | Kolosov et al. |
| 2010/0282005 A1 | * | 11/2010 | Kwon ..................... 73/865 |
| 2010/0291668 A1 | | 11/2010 | Bertrand et al. |
| 2011/0008776 A1 | | 1/2011 | Warthoe et al. |
| 2011/0269249 A1 | | 11/2011 | Warthoe et al. |
| 2011/0316522 A1 | | 12/2011 | Shinobu et al. |
| 2012/0190128 A1 | | 7/2012 | Nikbakht et al. |
| 2012/0304776 A1 | | 12/2012 | Novotny |
| 2014/0127826 A1 | | 5/2014 | Johal et al. |
| 2014/0154697 A1 | | 6/2014 | Johal et al. |

FOREIGN PATENT DOCUMENTS

| | | |
|---|---|---|
| WO | WO 2014/190240 A1 | 11/2014 |
| WO | WO 2014/190295 A2 | 11/2014 |
| WO | WO 2016/044055 A1 | 3/2016 |

OTHER PUBLICATIONS

U.S. Appl. No. 13/854,617, filed Apr. 1, 2013, Johal et al.
U.S. Appl. No. 13/872,577, filed Apr. 29, 2013, Johal et al.
International Patent Application No. PCT/US14/39397, filed May 23, 2014; International Search Report and Written Opinion dated Oct. 2, 2014; 14 pages.
International Patent Application No. PCT/US14/39397, filed May 23, 2014; International Preliminary Report on Patentability dated Nov. 24, 2015; 11 pages.
Waggoner et al., "Atomic Layer Deposited Silicon Dioxide Films on Nanomechanical Silicon Nitride Resonators" J Appl Phys, 2010; 107:114505. 5 pages.
Yang et al., "Effects of Diffusion Boundary Layer on Reaction Kinetics of Immunoassay in a Biosensor" J Appl Phys, Apr. 28, 2008; 10:084702. 10 pages.
European Patent Application No. 14801619.9, filed Dec. 18, 2015; Supplementary European Search Report and Search Opinion dated Nov. 25, 2016; 11 pages.
Dickherber et al., "Development of Highly Sensitive Bulk Acoustic Wave Device Biosensor Arrays for Screening and Early Detection of Prostate Cancer" Annual Summary, Distribution Statement, Jan. 1, 2009; Atlanta GA, 271 pages.
Hu et al., "A Lateral Field Excited Liquid Acoustic Wave Sensor" IEEE Transactions on Ultrasonics, Ferroelectrics, and Frequency Control, Nov. 2004; 51(11):1373-80.
Taratula et al., "Stepwise functionalization of ZnO nanotips with DNA" Langmuir, Feb. 17, 2009; 25(4):2107-13. Abstract only, [retrieved on Dec. 12, 2016]. Retrieved from the Internet: <URL: https://www.ncbi.nlm.nih.gov/pubmed/19199718>; 2 pages.
Zhang, "ZnO Nanotip-Based Acoustic Wave Sensors" PhD Dissertation, Graduate School—New Brunswick, Rutgers, The State University of New Jersey, Jan. 2008; 174 pages.

* cited by examiner

SENSORS, METHODS OF MAKING AND DEVICES

RELATED APPLICATION

This application is a U.S. National Stage Application of International Application No. PCT/US2014/039397, titled SENSORS, METHODS OF MAKING AND DEVICES INCLUDING SAME, filed on May 23, 2014, which claims the benefit of U.S. Provisional Patent Application No. 61/826,884, filed on May 23, 2013, each of which is hereby incorporated by reference in its entirety.

BACKGROUND

There are numerous instruments and measurement techniques for diagnostic testing of materials related to medical, veterinary medical, environmental, biohazard, bioterrorism, agricultural commodity, and food safety. Diagnostic testing traditionally requires long response times to obtain meaningful data, involves expensive remote or cumbersome laboratory equipment, requires large sample size, utilizes multiple reagents, demands highly trained users, and can involve significant direct and indirect costs. For example, in both the human and veterinary diagnostic markets, most tests require that a sample be collected from a patient and then sent to a laboratory, where the results are not available for several hours or days. As a result, the caregiver must wait to treat the patient.

Point of use (or point of care when discussing human or veterinary medicine) solutions for diagnostic testing and analysis, although capable of solving most of the noted drawbacks, remain somewhat limited. Even some of the point of use solutions that are available are limited in sensitivity and reproducibility compared to in laboratory testing. There is also often significant direct costs to a user as there can be separate systems for each point of use test that is available.

SUMMARY

Disclosed herein are sensors that include at least a first resonator, the at least first resonator having a first surface and an opposing second surface and the first resonator also having a bottom electrode; a piezoelectric layer; and a top electrode, wherein the piezoelectric layer is positioned between the bottom electrode and the top electrode; a metal oxide layer positioned on at least the second surface of the first resonator, the metal oxide layer having a thickness from about 10 Å to about 500 Å and the metal oxide layer comprising oxygen atoms; a silane layer, the silane layer comprising silicon atoms, the silicon atoms of the silane layer bound to oxygen atoms in the metal oxide layer; and a molecular recognition component layer, the molecular recognition component layer including molecular recognition components and the molecular recognition components bound to the silane layer.

Also disclosed are sensors that include at least a first and a second resonator, each of the first and second resonators having a first surface and an opposing second surface and each of the resonators having a bottom electrode; a piezoelectric layer; and a top electrode, wherein the piezoelectric layer is positioned between the bottom electrode and the top electrode; a Bragg reflector stack beneath the first surfaces of both the first and second resonators; and a molecular recognition component layer positioned adjacent the second surfaces of both the first and second resonators wherein the at least first and second resonators are connected in series.

Also disclosed are sensors that include at least a first and a second resonator, each of the at least first and second resonators having a first surface and an opposing second surface and each of the resonators having a bottom electrode; a piezoelectric layer; and a top electrode, wherein the piezoelectric layer is positioned between the bottom electrode and the top electrode; a coupling layer, the coupling layer; and a molecular recognition component layer, the molecular recognition component layer having a substantially circular shape and the molecular recognition layer including molecular recognition components that are bound to the coupling layer.

Also disclosed herein are sensors that include at least a first and a second resonator, each of the at least first and second resonator having substantially the same shape and each of the first and second resonators having a first surface and an opposing second surface and each of the resonators including: a bottom electrode; a piezoelectric layer; and a top electrode, wherein the piezoelectric layer is positioned between the bottom electrode and the top electrode; a metal oxide layer positioned on at least the second surface of both the first and second resonators, the metal oxide layer having a thickness from about 10 Å to about 500 Å and the metal oxide layer including oxygen atoms; a silane layer, the silane layer including silicon atoms, the silicon atoms of the silane layer bound to oxygen atoms in the metal oxide layer; and a molecular recognition component layer, the molecular recognition component layer including molecular recognition components bound to the silane layer, wherein the at least first and second resonators are connected in series.

Also disclosed are assemblies including at least one active sensor and at least one reference sensor. The at least one active sensor and at least one reference sensor can generally include bottom electrodes, piezoelectric layers and top electrodes. The assemblies can further include additional structures or components as discussed herein. The at least one reference sensor in disclosed assemblies includes a reference binding material layer over at least the reference sensor and the at least one active sensor includes a molecular recognition binding material layer over at least the active sensor.

Also disclosed are methods of forming sensors that include forming at least a first and a second resonator, the first and the second resonator each having a first surface and an opposing second surface, each of the first and second resonators having a bottom electrode; a piezoelectric layer on at least a portion of the bottom electrode; and a top electrode on at least a portion of the piezoelectric layer; and depositing a metal oxide layer on the second surface of both the first and second resonators, the metal oxide deposited using atomic layer deposition (ALD).

Also disclosed are methods of forming sensors that include forming at least a first and a second resonator, the first and the second resonator each having a first surface and an opposing second surface, each of the first and second resonators including a bottom electrode; a piezoelectric layer on at least a portion of the bottom electrode; and a top electrode on at least a portion of the piezoelectric layer; and forming a coupling layer on a second surface of at least the first and second resonators; and depositing a molecular recognition component composition on the coupling layer, the molecular recognition component deposited in a substantially circular shape that covers at least both the first and second resonators.

These and various other features will be apparent from a reading of the following detailed description and related drawings.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

Disclosed sensors can include at least one resonator (in some embodiments, at least two resonators) and various other structures that may be formed in association with the resonators. The at least one resonator in embodiments can include a bottom electrode, a piezoelectric layer, and a top electrode.

Figure 3:
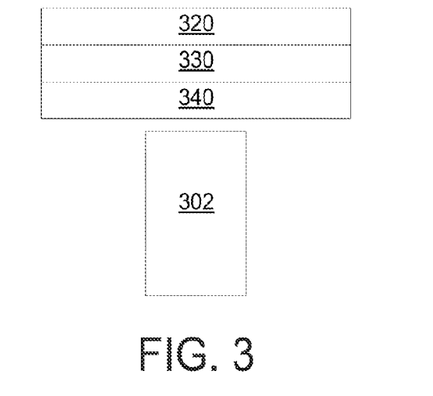
FIG. 3 depicts a cross section of an illustrative disclosed sensor.

In some embodiments disclosed sensors may include at least a first and second resonator, an oxygen containing layer on one surface thereof, a coupling layer on the oxygen containing layer and a molecular recognition layer on the coupling layer. FIG. 3 depicts an illustrative embodiment of a sensor 300 that includes a first resonator 302, an oxygen containing layer 340, a coupling layer 330, and a molecular recognition layer 320. In some embodiments, the oxygen containing layer may have a thickness as little as 10 Å, and in some embodiments not greater than 500 Å. In some embodiments, sensors can include at least a first resonator, the at least first resonator having a first surface and an opposing second surface and the first resonator including a bottom electrode; a piezoelectric layer; and a top electrode, wherein the piezoelectric layer is positioned between the bottom electrode and the top electrode; a metal oxide layer positioned on at least the second surface of the first resonator, the metal oxide layer having a thickness from about 10 Å to about 500 Å and the metal oxide layer including oxygen atoms; a silane layer, the silane layer including silicon atoms, the silicon atoms of the silane layer bound to oxygen atoms in the metal oxide layer; and a molecular recognition component layer, the molecular recognition layer including molecular recognition components and the molecular recognition components bound to the silane layer. In some embodiments, such sensors can include at least a second resonator as well, the second resonator including a bottom electrode; a piezoelectric layer; and a top electrode, wherein the piezoelectric layer is positioned between the bottom electrode and the top electrode Methods of forming such sensors are also disclosed herein. An illustrative method of forming a sensor can include forming at least a first and a second resonator, the first and the second resonator each having a first surface and an opposing second surface, each of the first and second resonators comprising a bottom electrode; a piezoelectric layer on at least a portion of the bottom electrode; and a top electrode on at least a portion of the piezoelectric layer; and depositing a metal oxide layer on the second surface of both the first and second resonators, the metal oxide deposited using atomic layer deposition (ALD). In some embodiments, the oxygen containing layer can be formed using atomic layer deposition (ALD), for example.

Disclosed herein are resonant sensors that can function as thin film bulk acoustic resonator (TFBAR) sensors. TFBAR sensors include a layer of piezoelectric material bounded on opposite sides by electrodes. The two surfaces of the sensor can undergo vibrational movement when the sensor is driven by a signal within the resonance band of the resonator. One surface of the resonator can be adapted to provide binding sites for an analyte of interest in samples to be analyzed. Binding of the material of interest on the surface of the resonator alters the resonant characteristics of the sensor. This alteration can be detected and analyzed to provide quantitative information regarding the analyte of interest. Generally resonant sensors provide better results when the bound material of interest is physically bound as close as possible to the sensor itself (piezoelectric material bounded on opposite sides by electrodes). For this reason sensors are generally fabricated by using the minimum possible material and/or layers necessary to afford binding of the analyte of interest.

Previously utilized sensors attached material that could bind a component of a sample of interest directly to the top electrode. Contrary to that, some embodiments of disclosed sensors can include at least one additional layer on top of the top electrode before the material that can bind a component of a sample of interest. In some embodiments, one of the additional layers can include oxygen atoms that can then be bound to a coupling layer to which a material capable of binding the material of interest can be bound. Surprisingly the addition of an additional layer between the top electrode and the, which moves the material of interest (e.g., the mass of that material of interest) farther away from the sensor does not diminish the signal provided by the sensor, and in some embodiments can actually provide a better signal from the sensor. It is thought but not relied upon that the oxygen containing layer disposed on the top electrode may provide rigidity to the sensor. Rendering the sensor more rigid could decrease the dampening of the resonance, thereby maintaining or even increasing the signal from the sensor.

Figure 4:
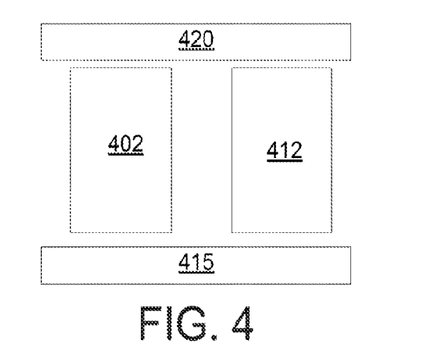
FIG. 4 depicts a cross section of an illustrative disclosed sensor.

In some embodiments disclosed sensors may include at least a first and a second resonator that are electrically connected in series, a Bragg reflector stack beneath the first and second resonators and a molecular recognition component layer above the first and second resonators. FIG. 4 depicts an illustrative embodiment of a sensor 400 that includes a first resonator 402, a second resonator 412, a Bragg reflector stack 415, and a molecular recognition layer 420. In some embodiments, the sensor can include at least at least a first and a second resonator, each of the first and second resonators having a first surface and an opposing second surface and each of the resonators having a bottom electrode; a piezoelectric layer; and a top electrode, wherein the piezoelectric layer is positioned between the bottom electrode and the top electrode; a Bragg reflector stack beneath the first surfaces of both the first and second resonators; and a molecular recognition component layer positioned adjacent the second surfaces of both the first and second resonators wherein the at least first and second resonators are connected in series.

First and second resonators having an adjacent configuration such as those depicted in FIG. 4 for example, may become coupled through the substrate on which they are formed. Such coupling can be considered undesirable. Utilization of an acoustic Bragg reflector stack may function to alleviate such coupling. Although reduction of such coupling by the Bragg reflector stack may be beneficial, the Bragg reflector stacks may create parasitic resonances. Connecting the first and second resonators in series can diminish or prevents the possible parasitic resonances. The electrical and mass loading effect of the first and second resonators connected in series can be as good as (in some embodiments, better than) a single resonator minus the Bragg reflector stack induced parasitic resonances.

Figure 5A:
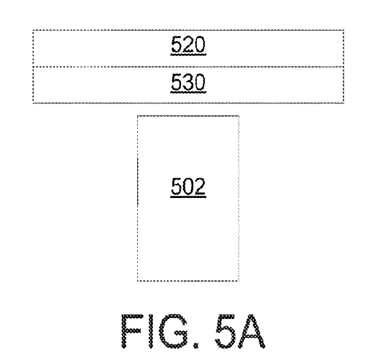
FIGS. 5A and 5B depict a cross section of an illustrative disclosed sensor (FIG. 5A) and a top down view (FIG. 5B).
Figure 5B:
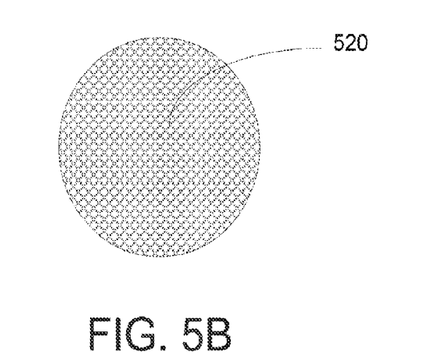

In some embodiments, disclosed sensors can include at least a first resonator, a coupling layer thereon and a molecular recognition component layer coupled to the coupling layer. FIGS. 5A and 5B depict a cross section and a top down view of an illustrative embodiment of a sensor 500 that includes a first resonator 502, a coupling layer 530, and a substantially circular molecular recognition layer 520. The substantially circular shape of the molecular recognition layer 520 can be seen especially in FIG. 5B. It should be noted that the at least first resonator in such embodiments can have any configuration, the molecular recognition component layer 520 can be overlying more than just at least a first resonator, for example at least a second resonator, or any combination thereof. In some embodiments, disclosed sensors can include at least a first resonator, the at least first resonator having a first surface and an opposing second surface and the resonator having a bottom electrode; a piezoelectric layer; and a top electrode, wherein the piezoelectric layer is positioned between the bottom electrode and the top electrode; a coupling layer, the coupling layer positioned adjacent the second surface of the at least first resonator; and a molecular recognition component layer, the molecular recognition component layer having a substantially circular shape and the molecular recognition component layer including molecular recognition components that are bound to the coupling layer.

Methods of forming such sensors are also disclosed herein. Illustrative methods can include forming at least a first resonator, the first resonator having a first surface and an opposing second surface, the first resonator having a bottom electrode; a piezoelectric layer on at least a portion of the bottom electrode; and a top electrode on at least a portion of the piezoelectric layer; and forming a coupling layer on a second surface of at least the first resonator; and depositing a molecular recognition component composition on the coupling layer, the molecular recognition component composition deposited so that a molecular recognition component layer having a substantially circular shape that covers at least the first resonator is formed.

The overall substantially circular shape of such sensors can be formed at least in part by the way in which the molecular recognition component layer (the material the analyte of interest binds to) can be formed. A substantially circular shape can afford the use of a minimum amount of a composition containing the molecular recognition component, because as a composition containing a molecular recognition component is deposited onto a sensor being formed in drop wise fashion, inherent surface/liquid interactions such as contact angle as well as surface tension may naturally provide a substantially circular shape as a solvent in the composition evaporates.

Any of the details disclosed herein (either following or preceding) regarding any of the particular portions or optional portions of disclosed sensors can be utilized as applicable in any of the above described types of sensors. Furthermore, assemblies or other disclosed devices can utilize any of the above disclosed types of sensors (optionally including any features discussed herein).

Disclosed sensors can be described by their overall shape. Disclosed sensors can have various shapes. In some embodiments, disclosed sensors can be square, rectangular, hexagonal, circular, or virtually any other shape. In some embodiments disclosed sensors can have a substantially circular shape. A single disclosed sensor can include at least two resonators. In some embodiments, the at least two resonators that are part of a single sensor can have substantially the same shape. In some embodiments, the at least two resonators can have different shapes In some embodiments, a single sensor can include at least two resonators configured in such a way that an overall shape of a region containing the at least two resonators can be used to describe the sensor and can be referred to as the configuration of the resonator(s). In some embodiments, the overall shape of a sensor and the configuration of the resonators can be the same and in some embodiments the overall shape of a sensor and the configuration of the resonators can be different. In some embodiments, the at least two resonators that are part of a single sensor can have the same substantially semicircular shape, providing an overall substantially circular resonator configuration, with the two, for example, substantially semicircularly shaped resonators configured with the flat sides of the semicircles facing each other. In some embodiments, four (4) resonators could be utilized in a sensor, for example, each of the four resonators being shaped like one fourth (¼) of a circle. The overall resonator configuration in such an embodiment could be described as substantially circular. In some embodiments, the at least two resonators can have at least two different shapes that when configured in a disclosed sensor form a substantially circular shape. For example, one resonator could be one quarter (¼) of a circle and the other resonator could be the other three quarters (¾) of the circle. The overall resonator configuration in such an embodiment could be described as substantially circular. In some embodiments, four (4) resonators, for example, having substantially square (or rectangular) shapes could be formed and configured into a larger substantially square (or rectangular) shape. The overall resonator configuration in such an embodiment could be described as square or rectangular. Embodiments having square (or rectangular) resonator configurations, for example, could have a substantially circular sensor shape. In embodiments where the sensor shape and the resonator configuration are different, the sensor shape can be dictated or controlled by the shape of the molecular recognition component layer (described below) formed thereon.

The overall substantially circular shape of some disclosed sensors can be formed at least in part by the way in which the molecular recognition component layer (the material the analyte of interest binds to) is formed. A substantially circular molecular recognition component layer shape can afford the use of a minimum amount of a composition containing the molecular recognition component because as a composition containing a molecular recognition component is deposited onto a sensor being formed in drop wise fashion, inherent surface/liquid interactions such as contact angle as well as surface tension may naturally provide a substantially circular shape.

In some embodiments a combination of a sensor having a substantially circular sensor shape (including for example two substantially semicircular shaped resonators) with an oxide layer and molecular recognition component layer formed thereon can provide TFBAR sensors that can be useful in larger systems for detecting and quantifying an analyte of interest in a sample.

Figure 1A:
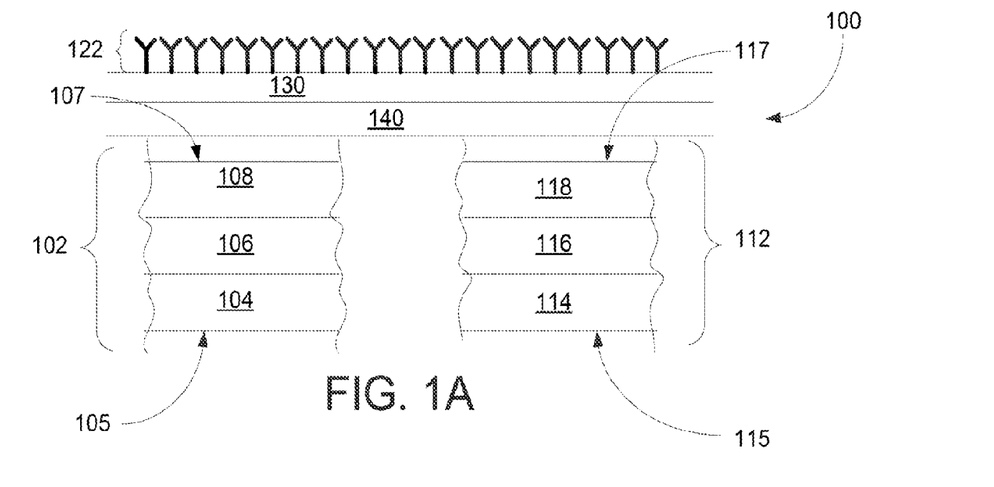
FIGS. 1A and 1B are schematic depictions of a cross section (FIG. 1A) and a top down view (FIG. 1B) of an illustrative disclosed sensor.
Figure 1B:
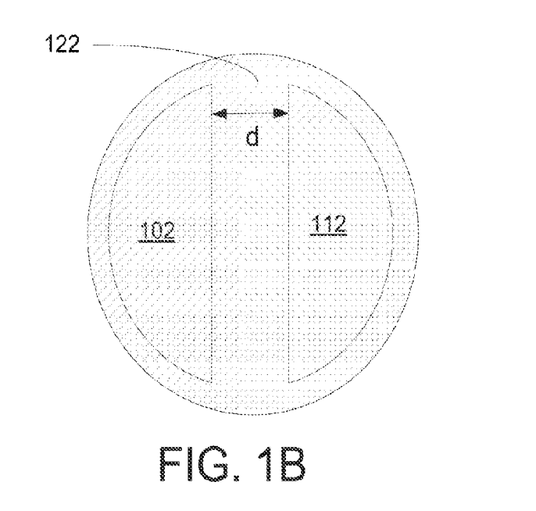

FIGS. 1A and 1B depict an illustrative disclosed sensor. Disclosed sensors can generally include at least a first and second resonator. Some disclosed sensors can also include an oxygen containing layer, a coupling layer, and a molecular recognition component layer. FIG. 1A shows an illustrative sensor 100. The illustrative sensor 100 includes a first resonator 102 and a second resonator 112. In some embodiments the first resonator 102 and the second resonator 112 can be substantially the same and in some embodiments they can be different in one or more than one respect. Each of the first resonator 102 and the second resonator 112 has a first surface 105 and 115 respectively and an opposing second surface 107 and 117 respectively. The first resonator 102 and the second resonator 112 may be located a distance apart. This distance is depicted as d in FIG. 1B. In some embodiments the first resonator 102 and the second resonator 112 may be spaced at least 1 micrometer (μm) apart (d), and in some embodiments they may be spaced at least 45 μm apart (d). In some embodiments the first resonator 102 and the second resonator 112 may be spaced not more than 100 μm (d), and in some embodiments they may be spaced not more than 75 μm apart (d). In some embodiments, the spacing between two resonators need not be constant; the spacing between two resonators need not be the same as the spacing between two other resonators, or any combination thereof.

Each of the resonators for example, at least the first resonator 102 and the second resonator 112, can include a bottom electrode 104 and 114, a piezoelectric layer 106 and 116 and a top electrode 108 and 118. The piezoelectric layer 106 and 116 is positioned between the bottom electrode 104 and 114 and the top electrode 108 and 118. Additional layers not depicted in FIG. 1A can also be interspersed between, above, below, or some combination thereof the noted layers.

It should be noted that the bottom electrode 104 and 114 of the first resonator 102 and 112 can be part of a single layer. The same can be said for the piezoelectric layer 106 and 116 and the top electrode 108 and 118. This implies that the bottom electrodes (or one or two of the bottom electrodes, the top electrodes, and the piezoelectric layers) of the at least two resonators can have a bottom electrode (or other combination) that is shared or the bottom electrodes (or other combination) can be distinct but formed from a single material layer. In embodiments where the first resonator 102 and the second resonator 112 include at least two structures (bottom electrode, piezoelectric layer, or top electrode) that are formed from a single material layer, the material layers forming the distinct structures need not exist across the entire larger device housing the sensor (if such a larger construct exists). For example a sensor could include bottom electrodes 104 and 114 that are formed from a single layer of material; and piezoelectric layers 106 and 116 that are formed from a single layer of material. The layers that form the bottom electrodes and the piezoelectric layers respectively need not be entirely congruous. For example portions of the piezoelectric material could be removed at various locations across the sensor. It should also be noted that disclosed resonators such as the first and second resonator 102 and 112 are formed only at locations where bottom electrode material and top electrode material overlap with piezoelectric material therebetween. In some embodiments the bottom electrode 104 and 114, the piezoelectric layer 106 and 116 and the top electrode 108 and 118 can all be formed from a single deposited layer of bottom electrode material, piezoelectric material, and top electrode material respectively. It should also be noted that in some embodiments, a plurality of bottom electrodes, top electrodes, piezoelectric layers, or any combination thereof for a plurality of resonators can be entirely freestanding forming freestanding resonators, but could have been formed from a single layer of material. It should also be noted that each of or any of the bottom electrode, the piezoelectric layer, and the top electrode could have shapes that are different than any of the others.

The at least first and second resonators 102 and 112 can be made of various materials. In some embodiments the bottom electrode 104 and 114 can be made of the same material. Illustrative materials for the bottom electrode 104 and 114 can include for example, aluminum (Al), gold (Au), tungsten (W), copper (Cu), molybdenum (Mo), and tantalum (Ta). In some embodiments the bottom electrode 104 and 114 can both include aluminum. In some embodiments the top electrode 108 in 118 can be made of the same material. Illustrative materials for the top electrode 108 and 118 can include for example, Au, Al, W, Cu, Mo, and Ta. In some embodiments the top electrode 108 and 118 can both include gold. In some embodiments the piezoelectric layer 106 and 116 can be made of the same material. Illustrative materials for the piezoelectric layer 106 and 116 can include for example aluminum nitride (AlN), zinc oxide (Zn), and lead zirconate titanate (PZT). In some embodiments the piezoelectric layer 106 and 116 can both include aluminum nitride.

In some embodiments, the at least first and second resonators 102 and 112 can be described as having substantially the same shape. In some embodiments the first and second resonators can each be described as having a semicircular shape. FIG. 1B depicts a top down view of an illustrative sensor including a first resonator 102 and a second resonator 112 both having a substantially semicircular shape. The sensor 100 can be described as having a substantially circular resonator configuration, with the two semicircular shaped resonators 102 and 112 configured to form the substantially circular resonator configuration. The sensor 100 can also be described as having a substantially circular sensor shape because the molecular recognition component layer 122 (discussed below) has a substantially circular shape.

In particularly illustrative embodiments a substantially semicircular shape of each of the first and second resonators 102 and 112 can be formed by top electrode layers 108 and 118 that share a substantially circular shaped material layer and bottom electrode layers 108 and 118 that are both independently substantially semicircular and distinct (e.g., a circle of bottom electrode material with a gap spanning the diameter of the circle, the gap having a width d). Layers of top electrode, piezoelectric, bottom electrode, or any combination thereof materials can be patterned to provide any desired shapes, including for example semicircular shapes, circular shapes, square shapes, rectangular shapes, or otherwise using known methods including lithography methods for example.

In some embodiments, the at least first resonator 102 and the second resonator 112 (and additional resonators if present) can be electrically connected to each other in series. It is noted that the electrical connections of the two or more resonators are not depicted in the attached figures. One of skill in the art having read the specification will understand and know how to connect at least the first resonator 102 and the second resonator 112 in series. The serial connection of the at least first resonator 102 and the second resonator 112 generally makes a signal received therefrom as if it was received from a single resonator.

A quantitative and qualitative understanding of the Q of a resonator may be obtained by plotting on a Smith Chart, the ratio of the reflected energy to applied energy (i.e., the reflection coefficient) as the frequency is varied for the case in which one electrode is connected to ground and another to signal, for an SMR resonator with an impedance equal to (or normalized to) the system impedance at the resonant frequency. As the frequency of the applied energy (e.g., RF signal) is increased, the magnitude/phase of the SMR resonator sweeps out a circle in a clockwise fashion on the Smith Chart. This is referred to as the Q-circle. Where the Q-circle first crosses the real axes (horizontal axes), this corresponds to the series resonance frequency $f_s$. The real impedance (as measured in Ohms) is $R_s$. As the Q-circle continues around the perimeter of the Smith chart, it again crosses the real axes. The second point at which the Q circle crosses the real axis is labeled $f_p$, the parallel or anti-resonant frequency of the SMR. The real impedance at $f_p$ is $R_p$.

Often it is desirable to minimize $R_s$ while maximizing $R_p$. Qualitatively, the closer the Q-circle "hugs" the outer rim of the Smith chart, the higher the Q-factor of the device. The Q-circle of an ideal lossless resonator would have a radius of one and would be at the edge of the Smith chart.

Among other adverse effects, lateral modes deleteriously impact the quality (Q) factor of a BAW resonator device. In particular, the energy of Rayleigh-Lamb modes is lost at the inactive region and at the interfaces of the BAW resonator device. As will be appreciated, this loss of energy to spurious modes is a loss in energy of desired longitudinal modes, and ultimately a degradation of the Q-factor. Smith Charts can be used to compare spurious modes of resonators.

Figure 6A:
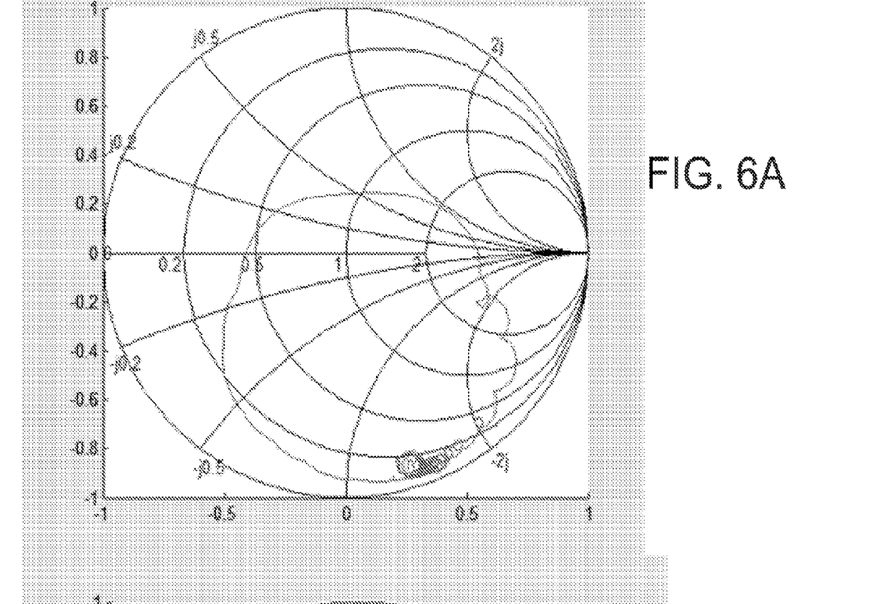
FIGS. 6A to 6D are Smith plots plots for various resonators.
Figure 6B:
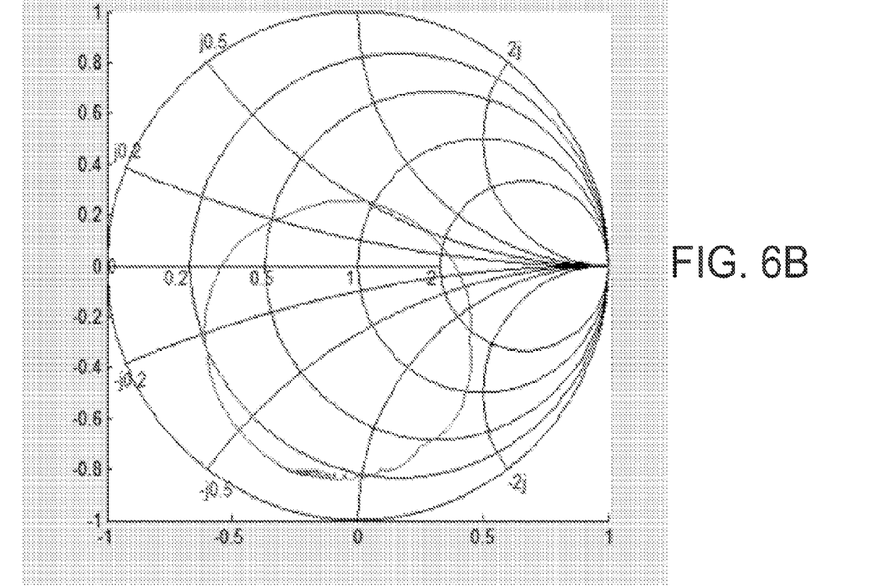
Figure 6C:
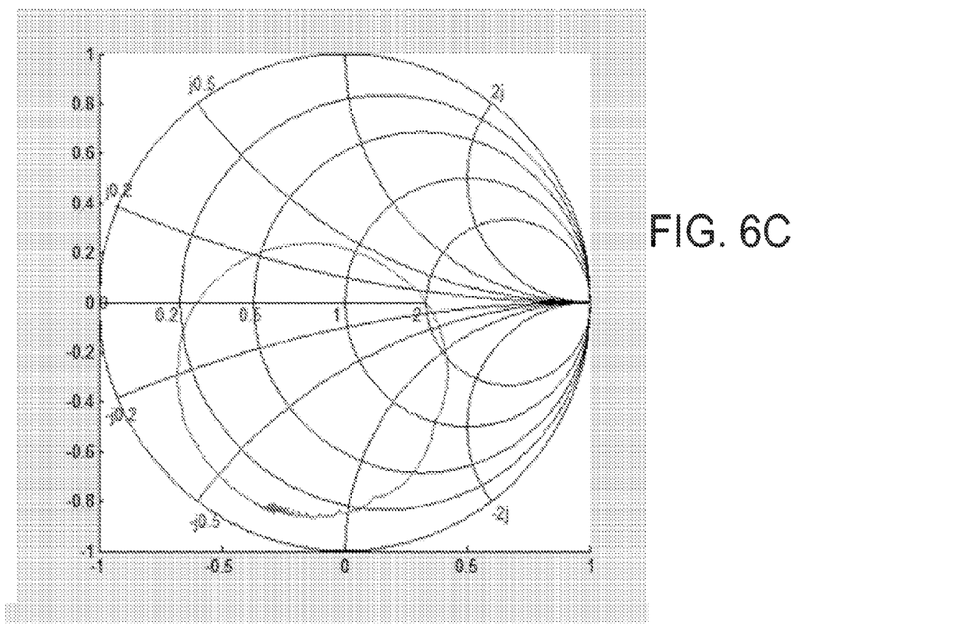
Figure 6D:
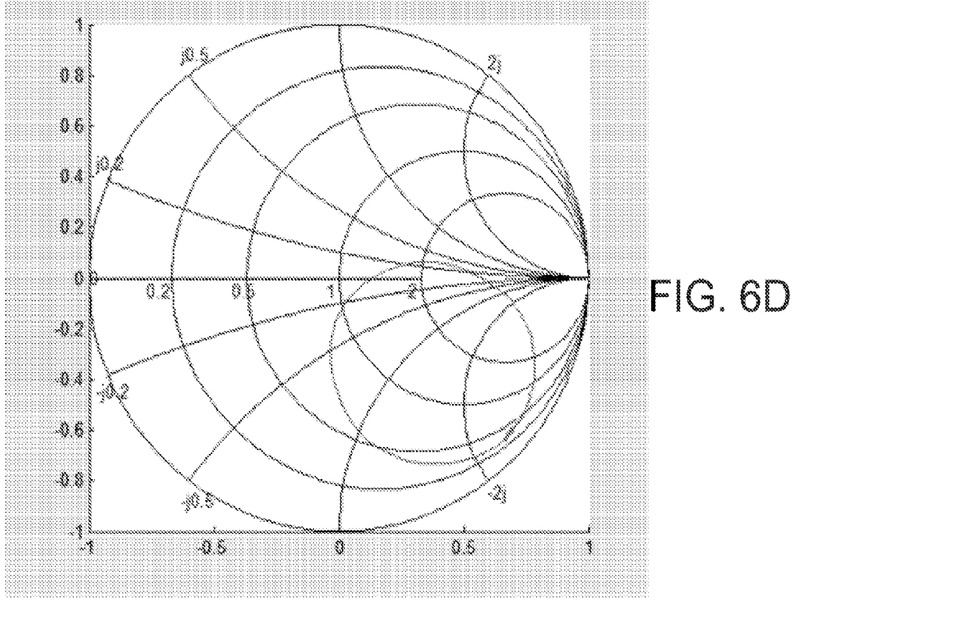

FIGS. 6A to 6D shows Smith plots for various resonators. The resonators which generated the Smith plots seen in FIGS. 6A to 6D are the same except for the characteristics noted herein. All of the resonators had a AlN piezoelectric layer. FIG. 6A shows the Smith plot of a circular 900 MHz resonator have a 350 µm diameter. Spurious resonance is apparent as seen from the many loops in the plot. FIG. 6B shows the Smith plot of two circular 2,250 MHz resonators connected in series. Each resonator had a diameter of 213 µm and there was 42 µm between the two. Spurious resonance was significantly reduced in comparison to the resonator of FIG. 6A with only a single circular resonator. FIG. 6C shows the Smith plot of two semicircular 2,250 MHz resonators connected in series. The resonators were placed flat sides facing with a 48 µm gap and the overall circular resonator configuration was circular with a 350 µm diameter. Spurious resonance was reduced in comparison to both the resonators of FIGS. 6A and 6B. FIG. 6D shows the Smith plot of four square 2,250 MHz resonators connected in series. Each resonator had a length and width of 125 µm. The four resonators were configured in a square shape with 42 µm gap between each resonator. Spurious resonance was reduced in comparison to all of the resonators of FIGS. 6A, 6B, 6C and 6D.

In some embodiments, disclosed sensors can also include an oxygen containing layer. The sensor 100 depicted in FIG. 1A includes oxygen containing layer 140 positioned on the second surface 107 and 117 of the first and second resonators 102 and 112. In some embodiments the oxygen containing layer 140 can exist across substantially the entire sensor. In some embodiments an oxygen containing layer can have a thickness that is at least 10 Å, at least 50 Å, at least 75 Å, or at least 95 Å. In some embodiments a metal oxide layer can have a thickness that is not greater than 500 Å, not greater than 200 Å, not greater than 125 Å, or not greater than 105 Å.

An oxygen containing layer can include oxygen atoms, compounds including oxygen atoms, or both. In some embodiments an oxygen containing layer can be an oxide layer, or more specifically a metal oxide layer and can include any metal oxide. In some embodiments the metal oxide layer can include $TiO_2$, $SiO_2$, $Al_2O_3$, or ZnO. In some embodiments the metal oxide layer can include $TiO_2$. A metal oxide layer can be described as including oxygen atoms. The oxygen atoms can function to chemically bond or bind material of a layer deposited thereon.

An oxygen containing layer can be deposited using various methods. In some embodiments an oxygen containing layer can be deposited using atomic layer deposition (ALD). ALD can provide oxide layers that are relatively thin, relatively uniform, relatively dense, or some combination thereof. ALD can be described as a self-limiting process that builds films of material in layers and can therefore repeatably produce uniform and very thin films.

A sensor can also include a coupling layer. The sensor 100 disclosed in FIG. 1A includes a coupling layer 130. The coupling layer 130 can generally be described as positioned over the oxygen containing layer 140. In some embodiments the coupling layer can exist across substantially the entire sensor 100. In some embodiments, the coupling layer can be described as a monolayer of the compound making up the coupling layer. In some embodiments, the coupling layer 130 can have a thickness that is at least 10 Å, or at least 20 Å. In some embodiments the coupling layer 130 can have a thickness that is not greater than 100 Å, or not greater than 50 Å.

In some embodiments the coupling layer 130 can be more specifically described as a silane layer or including a silane containing component. The silane layer can more specifically be described as being made up of silane coupling agents. Silane coupling agents are silicon-based chemicals that contain both inorganic reactivity and organic reactivity in the same molecule. A general structure can be described as $(RO)_3SiCH_2CH_2CH_2—X$, where RO represents the inorganic reactivity group or a hydrolyzable group (for example, methoxy, ethoxy, acetoxy, thiol, or aldehyde) and X represents a group containing an organic reactivity group (for example, amino, methacryloxy, or epoxy) and X can also include additional carbons (—$(CH_2)_n$) and may or may not include functional groups. In sensor 100 a silane layer 130 can function to couple the metal oxide layer 140 to the molecular recognition component layer 122.

Illustrative materials that can be utilized to form a silane layer 130 can include for example (3-Aminopropyl)triethoxysilane, (3-Aminopropyl)trimethoxysilane, (3-Glycidyloxypropyl)trimethoxysilane, (3-Glycidyloxypropyl)triethoxysilane, (3-Mercaptopropyl)trimethoxysilane, (3-Mercaptopropyl)triethoxysilane, Trimethoxy[2-(7-oxabicyclo[4.1.0]hept-3-yl)ethyl]silane, Triethoxy[2-(7-oxabicyclo[4.1.0]hept-3-yl)ethyl]silane, Trimethoxysilyl Alkyl, and AldehydeTriethoxysilyl Alkyl Aldehyde. In some embodiments a silane layer 130 can be formed with (3-Glycidyloxypropyl)triethoxysilane for example.

A sensor can also include a molecular recognition component layer. The sensor 100 disclosed in FIG. 1A includes a molecular recognition component layer 122. The molecular recognition component layer 122 can generally be described as positioned adjacent the at least first and second resonators, and can more specifically be described as positioned over the coupling layer 130. In some embodiments the molecular recognition component layer 122 can exist across substantially the entire sensor 100. In some embodiments, the molecular recognition component layer 122 can have a thickness that is at least 5 Å, or at least 50 Å. In some embodiments the molecular recognition component layer 122 can have a thickness that is not greater than 2000 Å, or not greater than 250 Å.

The molecular recognition component layer 122 can include any material capable of interacting with an analyte of interest in such a way that would allow the analyte of interest to be analyzed. The molecular recognition component could include any component that selectively binds to the analyte of interest. By way of example, the molecular recognition component may be selected from the group consisting of nucleic acids, nucleotide, nucleoside, nucleic acids analogues such as PNA and LNA molecules, proteins, peptides, antibodies including IgA, IgG, IgM, IgE, lectins, enzymes, enzymes cofactors, enzyme substrates, enzymes inhibitors, receptors, ligands, kinases, Protein A, Poly U, Poly A, Poly lysine, triazine dye, boronic acid, thiol, heparin, polysaccharides, coomassie blue, azure A, metal-binding peptides, sugar, carbohydrate, chelating agents, prokaryotic cells and eukaryotic cells. In some embodiments, antibodies can be utilized as the molecular recognition component, and in such embodiments, the thickness of the molecular recognition component layer 122 can be described as not less than 100 Å, or in some embodiments not less than 150 Å.

The molecular recognition component layer 122 can be formed on (or more specifically bound to) the coupling layer 130 using known techniques. One or more than one individual elements or chemical groups (containing two or more elements) components in the molecular recognition component layer can each be chemically bonded to, for example, a silane or more than one silane in the coupling layer 130. Conditions and process steps for affecting this binding would be known to one of skill the art reading the specification. It should also be noted that molecular recognition components could be bound to the coupling layer through additional coupling agents or compounds other than just the coupling layer itself. In some embodiments, an antibody can be utilized as a molecular recognition component and it can be bound to an epoxy silane containing coupling layer.

In some embodiments, a molecular recognition component layer 122 can have a substantially circular shape. The molecular recognition component layer 122 can generally be described as covering both the at least first and second resonators 102 and 112. The shape of the molecular recognition component layer 122 can in part define the shape of the sensor 100 (in combination with or in light of the resonator configuration as discussed above). In some embodiments, a molecular recognition layer can be of a shape that is designed to at least cover the entire surface overlying the regions of the at first and second resonators. In some embodiments, a molecular recognition component layer can be of a shape that covers more than the entire surface overlying regions of the at least first and second resonators. In some embodiments, the substantially circular shape of a molecular recognition component layer can be due at least in part to the process that forms the layer. Details of such process are described below.

As mentioned above, first and second resonators 102 and 112 may optionally include layers not depicted in FIG. 1A. For example, layers designed to promote adhesion between two layers, layers designed to protect structures, layers, or materials, layers designed to provide other functions, or any combination thereof may optionally be included in first and second resonators.

A specific example of an optional additional layer can include an adhesion layer for example. For example an adhesion layer can be formed on the surface of the piezoelectric layers 106 and 116. In some embodiments, an adhesion layer if included may function to improve adhesion between the top electrode material and the piezoelectric layers. In some embodiments, an adhesion layer if included may include materials that are compatible with the material of the top electrode layer, the material of the piezoelectric layer, or both. Illustrative specific materials that can be used for the adhesion layer can include for example titanium (Ti), or chromium (Cr). In some embodiments where the top electrode is gold, an optional adhesion layer may include Ti or Cr, for example. In some embodiments, an adhesion layer if included may have a thickness of at least 100 Å, at least 200 Å, or at least 250 Å. In some embodiments an adhesion layer if included may have a thickness of not greater than 500 Å, not greater than 400 Å, or not greater than 350 Å. In some embodiments an adhesion layer if included may have a thickness of about 300 Å.

Illustrative sensors may also include optional components not discussed above. For example, in some embodiments a sensor may include a Bragg reflector stack. In some embodiments, a Bragg reflector stack if included may be disposed beneath the bottom electrodes 104 and 114 of at least both the first and second resonators. First and second resonators having an adjacent configuration such as that utilized in disclosed sensors may become coupled through the substrate on which they are formed. Such coupling may be considered undesirable. Utilization of an optical Bragg reflector stack may function to alleviate such coupling. Although reduction of such coupling by the Bragg reflector stack may be beneficial, the Bragg reflector stacks may create parasitic resonances. Connecting the first and second resonators in series to diminishes or prevents the possible parasitic resonances. The electrical and mass loading effect of the first and second resonators connected in series can be as good as (in some embodiments, better than) a single resonator minus the Bragg reflector stack induced parasitic resonances.

Figure 2A:
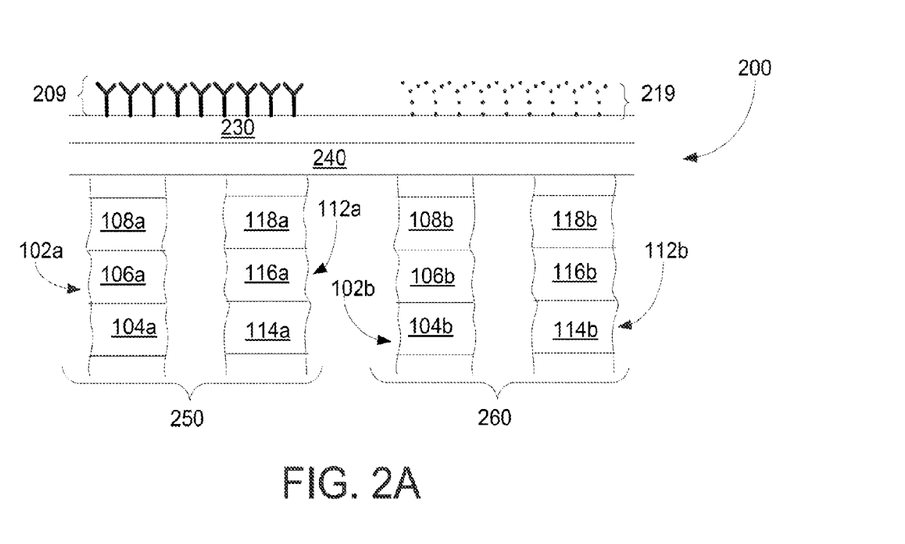
FIGS. 2A and 2B are schematic depictions of a cross section (FIG. 2A) and a top down view (FIG. 2B) of an illustrative disclosed assembly including disclosed sensors.

Also disclosed herein are assemblies or devices. Disclosed assemblies can generally include at least one active sensor and at least one reference sensor. In some embodiments, an assembly can include at least one reference sensor and two or more active sensors. Such embodiments may be beneficial because the two or more active sensors would be able to all utilize the reference sensor. In some embodiments, an assembly could include one reference sensor and at least three (for example) active sensors. FIG. 2 depicts an assembly 200, this illustrative assembly 200 includes an active sensor 250 and a reference sensor 260. The active sensor 250 includes a first resonator 102a and a second resonator 112a. The reference sensor 260 also includes a first resonator 102b and a second resonator 112b. The first resonator 102a, the second resonator 112a, the first resonator 102b and the second resonator 112b, all include bottom electrodes (104a, 114a, 104b, 114b), piezoelectric layers (106a, 116a, 106b, and 116b) and top electrodes (108a, 118a, 108b, and 118b). Characteristics of the resonators, such as the bottom electrodes, the piezoelectric layers, and the top electrodes can include those described above.

Figure 2B:
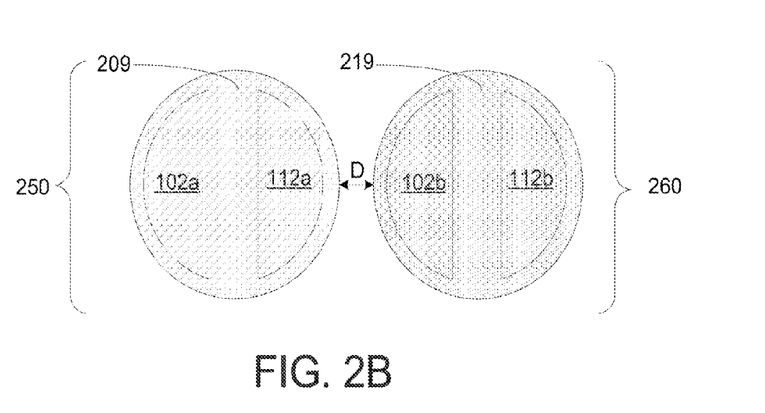

In some embodiments, the at least one active sensor 250 and the at least one reference sensor 260 can, but need not, have substantially the same shape. In some embodiments the active sensor 250 and the reference sensor 260 can both have substantially circular sensor shapes. The at least one active sensor 250 and the at least one reference sensor 260 can be a distance apart. FIG. 2B depicts the active sensor 250 and the reference sensor 260 as being a distance D apart. In some embodiments the active sensor 250 and the reference sensor 260 can be a distance (D) apart of at least 20 µm. In some embodiments the active sensor 250 and the reference sensor 260 can be a distance (D) apart of at least 50 µm. In some embodiments the active sensor 250 and the reference sensor 260 can be a distance (D) apart of not greater than 2000 µm. In some embodiments the active sensor 250 and the reference sensor 260 can be a distance (D) apart of not greater than 500 µm. In some embodiments that include one active sensor and one reference sensor, the two may be a distance (D) apart from 150 µm to 250 µm, for example about 200 µm apart.

An assembly 200 can also include an oxygen containing layer 240 and a coupling layer 230. These layers can be substantially as described above. In some embodiments, the oxygen containing layer 240 and the coupling layer 230 may cover more than just the at least one active sensor 250 and the at least one reference sensor 260. In some embodiments, the oxygen containing layer 240 and the coupling layer 230 may cover substantially the entire surface of at least a portion of a substrate upon which the at least one active sensor 250 and the at least one reference sensor 260 are located. Characteristics of the oxygen containing layer 240 and the coupling layer 230 can include those described above.

An assembly 200 can also include a molecular recognition component layer 209. In some embodiments, the molecular recognition component layer 209 can cover only an area located over the at least one active sensor 250. In some embodiments, a molecular recognition component layer 209 can cover more than the area overlying the at least one active sensor 260 but is not over the area overlying any of the at least one reference sensors 260. In some embodiments the molecular recognition component layer 209 can at least in part define the shape of the active sensor 250, for example a substantially circular shape. Characteristics of the molecular recognition component layer can include those described above.

An assembly 200 can also include a reference binding material layer 219. In some embodiments, the reference binding material layer 219 can cover only an area located over the reference sensor 260. In some embodiments, a reference binding material layer 219 can cover more than the area overlying the at least one reference sensor 250 but is not over the area overlying any of the at least one active sensors 250. In some embodiments the reference binding material layer 219 can at least in part define the shape of the reference sensor 260. The material that forms the reference binding material layer 219 can be chosen such that materials in a sample to be tested do not bind appreciably to the reference binding material layer material. In some embodiments the material that forms the reference binding material layer 219 can have a molecular weight that is substantially similar to that of the material that forms the molecular recognition component layer 209. In some embodiments a material that forms the reference binding material layer is a material which does not bind appreciably to any material in a sample to be tested and has a molecular weight that is substantially similar to that of the material that forms the molecular recognition component layer. Such embodiments should provide signals from the active sensor 250 and the reference sensor 260 that differ only due to the analyte of interest in the sample.

The particular type of reference binding material that is utilized to make a reference binding material layer can depend at least in part on the particular type of molecular recognition component that is utilized for the molecular recognition component layer. One of skill in the art having read this specification will be able to discern possible types of reference binding materials for particular molecular recognition components being utilized. In some embodiments where an antibody is being used as a molecular recognition component, a reference binding material could include for example, a comparable species/subtype of antibody with no known specificity or specificity towards a material known to be absent in the sample to be tested.

Also disclosed herein are methods of forming sensors. Illustrative methods can include forming at least a first and a second resonator, depositing an oxygen containing layer on a surface of at least the first and second resonators, forming a coupling agent layer on the oxygen containing layer, and depositing a molecular recognition component on the coupling agent layer.

Also disclosed herein are methods of forming sensors. Illustrative methods can include forming at least a first resonator, the first resonator having a first surface and an opposing second surface; and forming a coupling layer on a second surface of at least the first resonator; and depositing a molecular recognition component composition on the coupling layer, the molecular recognition component composition deposited so that a molecular recognition component layer having a substantially circular shape that covers at least the first resonator is formed. A composition containing the molecular recognition component can further include a solvent or other constituent designed to modulate the pH of the solution, stabilize the protein in either the liquid and dried state, or some combination thereof for example. A composition containing the molecular recognition component can further include other optional materials, including for example buffers, salts, sugars, other constituents to help stabilize the molecular recognition component, or any combination thereof. The solvent, once the composition containing the molecular recognition component is deposited can simply be allowed to evaporate based on its vapor pressure or conditions can be controlled to control (temperature control, humidity control, etc.) the rate of evaporation of the solvent.

In some embodiments the at least first and second resonators can be formed on a substrate, or more specifically in some embodiments a silicon wafer. Any methods utilized to deposit materials such as those discussed herein for the bottom electrode, the piezoelectric layer and the top electrode may be utilized to form the bottom electrode, the piezoelectric layer, and the top electrode. Illustrative types of methods can include vapor deposition methods (e.g., chemical vapor deposition methods [such as plasma enhanced chemical vapor deposition (PECVD) methods for example], physical vapor deposition methods), sputtering methods (e.g., reactive sputtering methods), atomic layer deposition (ALD) methods, and plating methods (e.g. electrochemical or electroless), for example. Furthermore, any methods utilized to pattern or shape layers may also be utilized herein. Illustrative types of methods can include lithography methods (e.g., photolithography), etching methods, (e.g., milling, reactive ion etching, chemical etching), and lift off techniques for example. First and second resonators formed herein can include characteristics such as those discussed above. As discussed above each of the first and second resonators include a first surface and an opposing second surface.

A next step can include depositing an oxygen containing layer, for example an oxide layer on at least the first and second resonators. More specifically for example, an oxide layer can be deposited on the second surface of both the first and second resonators. In some embodiments a single layer can be formed on the second surface of both the first and second resonators. In some embodiments more than one layer can be formed to cover the second surface of both the first and second resonators. In some embodiments a single deposition step can form a disclosed oxide layer, and in some embodiments more than one deposition step can be utilized to form a disclosed oxide layer.

In some embodiments step of depositing an oxide layer can be accomplished using atomic layer deposition (ALD). ALD is generally considered a thin film deposition technique that employs sequential gas phase chemical processes. ALD processes generally utilize precursors, and by exposing the surface to be coated sequentially to the precursors, the layer is grown on the surface. Because the surface is exposed to the precursors in a sequential manner, the deposition process is self-limiting and therefore relatively easy to control deposition depth. In some embodiments where $TiO_2$ is being deposited, precursors such as titaniumtetraisopropoxide (TTIP) or tetrakis-dimethyl-amino-titanium (TDMAT) can be utilized, for example.

A next step can include forming a coupling layer on the oxide layer. Formation of a coupling layer on the oxide layer can generally include depositing a composition including a coupling agent onto the oxide layer. Conditions that may or may not be required for the coupling agent to react with the oxide layer may depend at least in part on the particular coupling agent utilized. In some embodiments, silane materials can be utilized as a coupling agent. Disclosed methods can also optionally include removing unbound coupling agent and other components of the composition. Such an optional step can be undertaken after the coupling agent has been given sufficient time, the proper conditions, or some combination thereof to react with the oxide layer. An optional step of removing unbound coupling agent and other components of the composition can be accomplished by for example washing the surface with a liquid that will not dissolve the coupling agent.

A next step can include forming a molecular recognition component layer on the coupling layer. Formation of a molecular recognition component layer on the coupling layer can generally include depositing a composition including a molecular recognition component onto the coupling layer. Conditions that may or may not be required for the molecular recognition component to react with coupling layer may depend at least in part on the particular coupling agent and the particular molecular recognition component utilized. Disclosed methods can also optionally include removing unbound molecular recognition component and other components of the composition. Such an optional step can be undertaken after the molecular recognition component has been given sufficient time, proper conditions, or some combination thereof to react with the coupling agent on the oxide layer surface. An optional step of removing unbound molecular recognition component and other components of the composition can be accomplished by for example washing the surface with a liquid that will not dissolve the molecular recognition component, the coupling agent, or both.

In some embodiments, methods disclosed herein can also include other optional steps. For example, disclosed methods can also include a step of electrically connecting the first and second resonators in series. One of skill in the art having read the specification will understand how to electrically connect the first and second resonators in series. In some embodiments an optional step of electrically connecting the first and second resonators in series can occur before deposition of oxide layer, for formation of a coupling agent layer, or before a molecular recognition component layer is deposited. In some embodiments an optional step of electrically connecting the first and second resonators in series can occur before deposition of an oxide layer.

Another example of an optional step that can be employed in disclosed methods can include a step of placing a wafer. As discussed above, sensors formed herein can be formed on a substrate, for example a wafer or more particularly in some embodiments, a silicon wafer. Deposition processes utilized to form disclosed sensors can often be more cost-effectively carried out by forming a plurality of sensors on a single silicon wafer. At any point in a method after which a plurality of first and second resonators are formed, the substrate upon which the plurality of first and second resonators are formed can be diced. In some embodiments individual portions of the substrate containing only a first and second resonator can be formed via dicing. In some embodiments individual portions of the substrate containing two first and second resonators, for example an active sensor and a reference sensor as discussed above, can be formed via dicing. In some embodiments an optional step of placing can occur before deposition of an oxide layer, before deposition of a coupling agent layer, or before deposition of a molecular recognition component layer. In some embodiments, an optional step of dicing can occur before deposition of an oxide layer.

Another example of an optional step that can be employed in disclosed methods can include a step of mounting the sensor on an electrical connection board. As discussed above, sensors formed herein can be formed on a substrate, for example a wafer or more particularly in some embodiments a silicon wafer. A wafer containing one or more sensors can be attached to an electrical connection board. An electrical connection board can also be referred to as a printed circuit board (PCB). Attachment of wafer containing one or more sensors can refer to a physical attachment (e.g., utilizing an adhesive for example), and electrical attachment (e.g., electrically connecting electrical contacts connected to the first and second resonators to electrical contacts on the electrical connection board via an conductive material), or a combination thereof.

An example of specific illustrative methods can include deposing a metal oxide layer, or more specifically, $TiO_2$, on a silicon wafer containing a plurality of resonant sensors using ALD via titaniumtetraisopropoxide (TTIP) or tetrakis-dimethyl-amino-titanium (TDMAT) precursors at about 120° to 180° C. The silicon wafer is then diced into portions containing both an active sensor and an adjacent reference sensor. After dicing, the substrate containing the two sensors can be assembled and electrically connected to a printed circuit board (PCB). The PCB mounted sensor is then cleaned via an oxygen plasma cleaning process. The cleaned PCB mounted sensor then has epoxy silane deposited thereon using vapor phase deposition (a more specific explanation of one method of carrying out this step can include evacuating a chamber, optionally raising the temperature of the chamber, allowing the epoxy silane to evaporate and saturate the environment of the chamber, and then allowing the epoxy silane to be deposited on the PCB mounted sensor). The epoxy silane coated PCB mounted sensor can then have an antibody containing buffered composition containing sucrose spotted thereon. The spotted PCB mounted sensor is then placed in a temperature controlled environment and held at about 37° C. for about 30 minutes.

In the preceding detailed description several specific embodiments of compounds, compositions, products and methods are disclosed. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a composition, product, method or the like, means that the components of the composition, product, method or the like are limited to the enumerated components and any other components that do not materially affect the basic and novel characteristic(s) of the composition, product, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

Thus, embodiments of two part assemblies are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

What is claimed is:

1. A sensor comprising:
   at least a first resonator, the at least first resonator having a first surface and an opposing second surface and the first resonator comprising:
   a bottom electrode;
   a piezoelectric layer; and
   a top electrode,
   wherein the piezoelectric layer is positioned between the bottom electrode and the top electrode;
   a metal oxide layer positioned on at least the second surface of the first resonator, the metal oxide layer having a thickness from about 10 Å to about 500 Å and the metal oxide layer comprising oxygen atoms;
   a coupling layer comprising silicon atoms, the silicon atoms of the coupling layer bound to oxygen atoms in the metal oxide layer; and
   a molecular recognition component layer, the molecular recognition layer comprising molecular recognition components and the molecular recognition components bound to the coupling layer.

2. The sensor according to claim 1, further comprising at least a second resonator.

3. The sensor according to claim 2, wherein the at least the first and second resonators are electrically connected in series.

4. The sensor according to claim 2, wherein the at least first and second resonators have substantially the same shape.

5. The sensor according to claim 4, wherein the at least first and second resonators have substantially semicircular shapes.

6. The sensor according to claim 4, wherein the at least first and second resonators have substantially rectangular shapes.

7. The sensor according to claim 1, wherein the metal oxide layer is selected from $TiO_2$, $SiO_2$, $Al_2O_3$, or $ZnO$.

8. The sensor according to claim 1 wherein the metal oxide layer has a thickness from about 75 Å to about 125 Å.

9. The sensor according to claim 1, wherein the metal oxide layer is deposited using atomic layer deposition.

10. The sensor according to claim 9, wherein the metal oxide layer is deposited over the entirety of the sensor.

11. The sensor according to claim 1, wherein the coupling layer comprises an epoxy silane.

12. The sensor according to claim 1, wherein the molecular recognition component is an antibody.

13. The sensor according to claim 1, wherein the sensor further comprises a Bragg reflector stack positioned beneath the bottom electrode of at least the first resonator.

* * * * *